US00PP22255P2

(12) United States Plant Patent
Laviana

(10) Patent No.: US PP22,255 P2
(45) Date of Patent: Nov. 15, 2011

(54) ***AJUGA* PLANT NAMED 'PINK LIGHTNING'**

(50) Latin Name: *Ajuga reptans*
Varietal Denomination: Pink Lightning

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 12/925,768

(22) Filed: Oct. 29, 2010

(51) Int. Cl.
*A01H 5/00* (2006.01)

(52) U.S. Cl. ..... Plt./401

(58) Field of Classification Search ..... Plt./401
See application file for complete search history.

*Primary Examiner* — Kent L Bell
(74) *Attorney, Agent, or Firm* — Penny J. Aguirre

(57) ABSTRACT

A new cultivar of *Ajuga* plant, 'Pink Lightning', characterized by its variegated foliage that is with gray-green centers and creamy white in color, its leaves that are rugose with wavy edges, its racemes of pink flowers with variegated bracts and its tight plant habit that slowly spreads by stolons.

2 Drawing Sheets

Botanical classification: *Ajuga reptans*.
Variety denomination: 'Pink Lightning'.

BACKGROUND OF THE INVENTION

The present invention relates to a new and distinct cultivar of *Ajuga* plant, botanically known as *Ajuga reptans* 'Pink Lightning' and will be referred to hereinafter by its cultivar name, 'Pink Lightning'. The new cultivar of *Ajuga* is a hardy herbaceous perennial grown for landscape use.

'Pink Lightning' was discovered in August of 2007 as a naturally occurring meristematic mutation of *Ajuga reptans* 'Purple Brocade' (not patented) in a container at the Inventor's nursery in Kensington, Conn.

Asexual reproduction of the new cultivar was first accomplished by basal stem cuttings in Kensington, Conn. in summer of 2008. Propagation by cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Pink Lightning' as a unique cultivar of *Ajuga*.

1. 'Pink Lightning' exhibits variegated foliage that is gray-green and creamy white in color.
2. 'Pink Lightning' exhibits leaves that are rugose with wavy edges.
3. 'Pink Lightning' exhibits racemes of pink flowers with variegated floral leaves.
4. 'Pink Lightning' exhibits a tight plant habit that slowly spreads by stolons.

The parent plant, 'Purple Brocade', differs from 'Pink Lightning' in having foliage that is green in color and non-variegated and in having flowers that are purple in color. 'Pink Lightning' can be most closely compared to other *Ajuga reptans* cultivars with variegated foliage; 'Silver Beauty, 'Silver Queen', and 'Burgundy Glow' (all three unpatented). 'Silver Beauty' and 'Silver Queen' are similar to 'Pink Lightning' in having variegated foliage that is gray-green and creamy white in color, however both cultivars differ in having flowers that are blue in color. 'Burgundy Glow' differs from 'Pink Lightning' in having foliage that is burgundy-rose to gray-green with limited creamy white variegation in color and in having flowers that are blue in color.

BRIEF DESCRIPTION OF THE DRAWINGS

The accompanying colored photographs illustrate the overall appearance and distinct characteristics of a two year-old plant the new *Ajuga* as grown outdoors in a one-gallon container In Kensington, Conn.

The photograph in FIG. 1 illustrates the foliage of 'Pink Lightning' and

Figure 1:
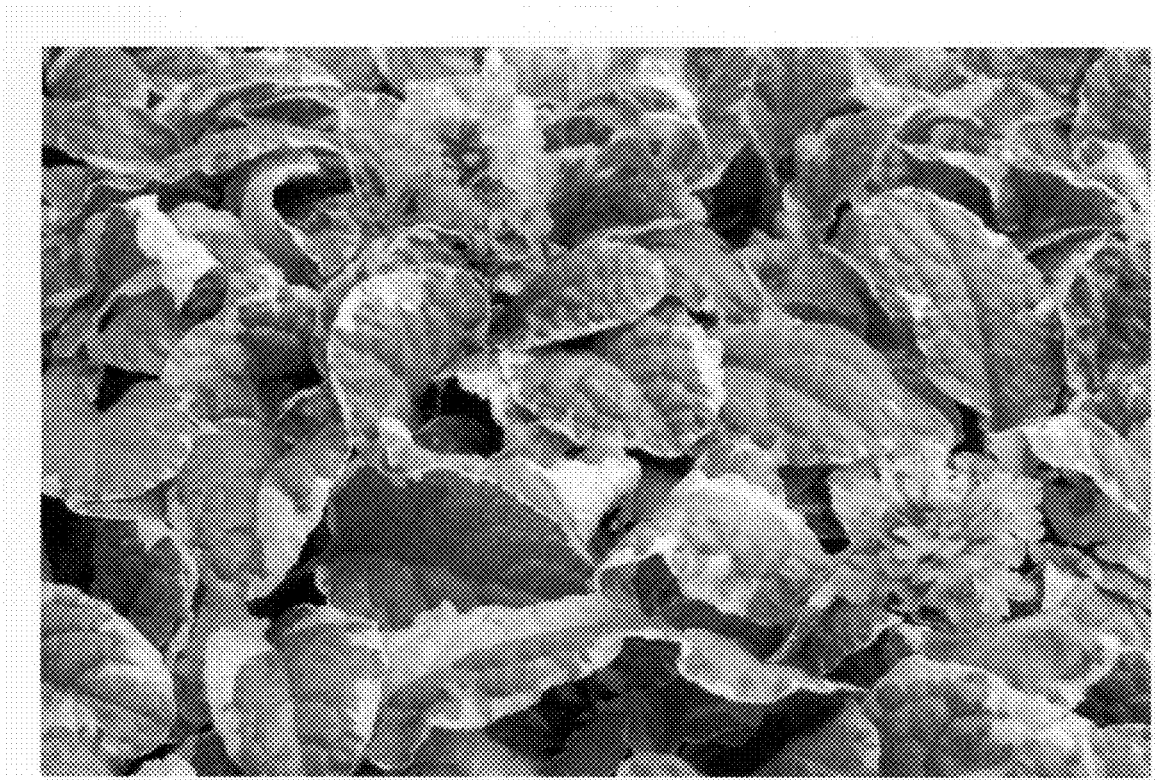
Figure 2:
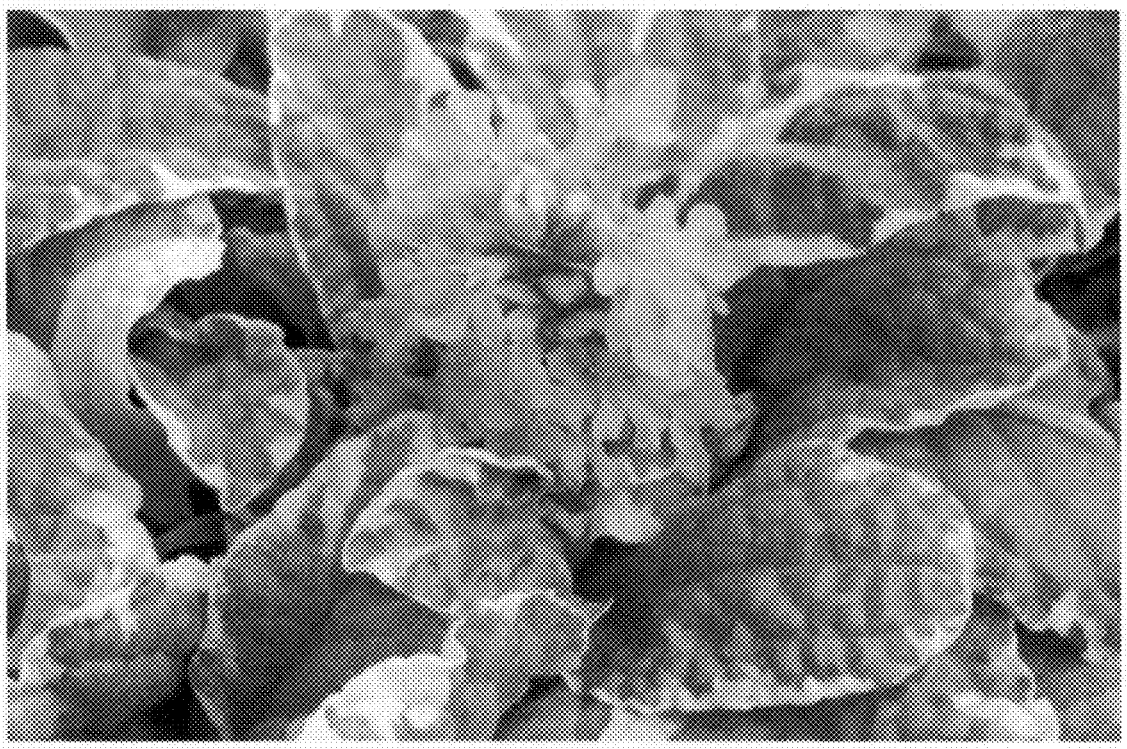

The photograph in FIG. 2 provides a close-up view of an inflorescence of 'Pink Lightning'.

The colors in the photograph may differ slightly from the color values cited in the detailed botanical description, which accurately describe the colors of the new *Ajuga*.

DETAILED BOTANICAL DESCRIPTION

The following is a detailed description of the new cultivar as observed on one year-old plants as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—About 4 weeks in spring in Connecticut.

*Plant habit.*—Herbaceous perennial, tightly compact and slowly spreading by stolons.

*Height and spread.*—Reaches about 7 cm in height (foliage) and about 20 cm in width.

*Hardiness.*—At least in U.S.D.A. Zones 4 to 9.

*Diseases and pests.*—Highly Disease and pest free under the conditions tested.

*Root description.*—Fibrous roots on short rhizomes, roots 158D in color, rhizomes about 1.5 cm in length and 3.5 mm in width, stolons 145B in color and about 1.5 mm in width.

*Branching habit.*—Basal rosettes of leaves from rhizomes.

*Propagation.*—Basal stem cuttings and division.

*Growth rate.*—Moderate.

Foliage description:

*Leaf shape.*—Spatulate.

*Leaf division.*—Simple.

*Leaf base.*—Truncate to base of rhizome.

*Leaf apex.*—Broadly acute to rounded.

*Leaf venation.*—Pinnate, color matches leaf color.

*Leaf margins.*—Lightly crenate, wavy and pubescent.

*Leaf attachment and arrangement.*—2-ranked from rhizome.

*Leaf orientation.*—Emerge upright and then slightly recurve, somewhat concave in relation to midrib.

*Leaf surface.*—Highly rugose between veins and finely puberulent on upper and lower surface.

*Leaf color.*—Upper surface, newly emerged foliage; centers 144B, margins 155A, lower surface; centers 138C, margins 155A; mature foliage upper surface; centers 138A, margins NN155A.

*Leaf size.*—Up to 8 cm in length and 5 cm in width in mid summer.

*Leaf quantity.*—Average of 16 per rhizome, about 300 in a clump 15 cm in diameter.

*Leaf attachment.*—Sessile.

Flower description:

*Inflorescence type.*—Raceme of dense whorls of bilabiate flowers.

*Inflorescence size.*—About 9 cm in height and 3 cm in width.

*Lastingness of inflorescence.*—Individual flowers last 2 to 3 days.

*Flower type.*—Bilabiate.

*Flower number.*—About 14 flowers per whorl, about 75 per raceme.

*Flower fragrance.*—None.

*Flower buds.*—Oblong in shape, about 8 mm in length and 2.5 mm in diameter, villose surface, color is 69B suffused at apex with 68B, color of calyx portion is 157A.

*Flower size.*—About 1.2 cm in length and about 7 mm in diameter.

*Peduncles.*—An average of 8 cm in length and 4 mm in width, color is a blend of 144D and 185C and becoming 75B towards the apex with ridges 186B, surface is villose.

*Pedicels.*—None, sessile.

*Calyx.*—5-pointed, star-shaped, about 5 mm in height and 4.5 mm in width, persistent.

*Sepals.*—5, elliptic in shape, about 5 mm in height and 2 mm in width with free portion about 2 mm in length, color is a blend of 145D and 69D with apex 70C on both surfaces, pubescent on both surfaces, margin is entire and villose.

*Petals.*—2, segments with very upper lip and a spreading lower lip with both segments fused into tube that is about 5 mm in length and 2 mm in width, upper lip is an extension of the tube (about 2 mm) and has a noticed apex, lower lip is slightly reflexed with 3 lobes; 2 oblong side lobes about 4 mm in length and 1.5 mm in width that spread sideways with a broadly acute apex and 1 center lobe that is about 6 mm in length and width, spatulate in shape and slightly reflexed with a rounded notched apex, all segments have entire margins, are pubescent on the outer surfaces and glabrous on the inner surfaces, color of inner surfaces is 62C with stripes and apex of N74C, color of tube and outer surfaces is a blend of NN155D, N74C and N74D.

*Bracts.*—2 per floral whorl, an average of 1.5 cm in length and 1.2 cm in width, ovate in shape, sessile, acute apex, truncate base, puberulent on both upper and lower surface, pubescent margins, color is the same as the mature leaves.

Reproductive organs:

*Pistils.*—1, style with stigma is about 8 mm in length, 0.5 mm in width, stigma; 2-branched, 1 mm in length, and 75C in color, style; 7 mm in length, 0.5 mm in width, and 75C in color, ovary; about 0.5 mm in diameter, N144B in color.

*Stamens.*—4, filament is about 8 mm in length, 0.5 mm in width and NN155C in color, anthers are oval in shape, about 1.5 mm in length and N200A in color, pollen is low in quantity and 14B in color.

*Fruit.*—Fruit and seed production was not observed under the conditions tested.

It is claimed:

1. A new and distinct variety of *Ajuga* plant named 'Pink Lightning' as described and illustrated herein.

* * * * *